United States Patent [19]

Hammesfahr et al.

[11] Patent Number: 5,304,586
[45] Date of Patent: Apr. 19, 1994

[54] RADIOPAQUE FLUORIDE RELEASING VLC DENTAL COMPOSITES AND THE USE OF SPECIFIC FILLERS THEREIN

[75] Inventors: Paul D. Hammesfahr, Wyoming, Del.; Paul S. Danielson, Corning, N.Y.; Robert C. Campbell, Harrington, Del.

[73] Assignee: Dentsply Research & Development Corp., Milford, Del.

[21] Appl. No.: 739,946

[22] Filed: Aug. 2, 1991

Related U.S. Application Data

[63] Continuation-in-part of Ser. No. 304,043, Jan. 30, 1989, abandoned.

[51] Int. Cl.$^5$ .......................... A61K 6/06; A61K 6/08
[52] U.S. Cl. .................................. 523/117; 523/116; 424/52; 501/59; 522/83; 522/96; 522/103; 522/908
[58] Field of Search .................. 424/52; 523/116, 117; 501/59

[56] References Cited

U.S. PATENT DOCUMENTS

| | | | |
|---|---|---|---|
| 3,331,731 | 7/1967 | Baak | 501/57 |
| 3,801,344 | 4/1974 | Dietz | 523/116 |
| 3,959,212 | 5/1976 | Rockett et al. | 523/117 |
| 4,032,504 | 6/1977 | Lee, Jr. et al. | 523/117 |
| 4,412,015 | 10/1983 | Lustgarten et al. | 523/117 |
| 4,491,453 | 1/1985 | Koblitz | 523/116 |
| 4,551,486 | 11/1985 | Tateosian et al. | 523/116 |
| 4,629,746 | 12/1986 | Michl et al. | 523/117 |
| 4,721,735 | 1/1988 | Bennett et al. | 523/116 |
| 4,738,722 | 4/1988 | Ibsen et al. | 523/116 |
| 4,746,686 | 5/1988 | Waller | 522/14 |
| 4,767,798 | 8/1988 | Gasser et al. | 523/117 |
| 4,772,325 | 9/1988 | Kwan et al. | 106/35 |
| 4,882,365 | 11/1989 | Gasser et al. | 523/117 |
| 4,900,697 | 2/1990 | Akahane et al. | 501/57 |
| 4,936,775 | 6/1990 | Bennett | 523/116 |

FOREIGN PATENT DOCUMENTS

| | | |
|---|---|---|
| 0049559 | 4/1982 | European Pat. Off. |
| 0102199 | 3/1984 | European Pat. Off. |
| 0047097 | 5/1986 | European Pat. Off. |
| 0238025 | 9/1987 | European Pat. Off. |
| 2610916 | 8/1988 | European Pat. Off. |
| 0380796 | 8/1990 | European Pat. Off. |
| 88/05652 | 8/1988 | PCT Int'l Appl. |
| 8805652 | 8/1988 | PCT Int'l Appl. |

OTHER PUBLICATIONS

R. L. Bowen and G. W. Cleek "A New Series of X-Ray Opaque Reinforcing Fillers for Composite Materials", Journal of Dental Research, Jan.-Feb. 1972, pp. 177-182.

*Primary Examiner*—Thurman K. Page
*Assistant Examiner*—Amy Hulina
*Attorney, Agent, or Firm*—Dale R. Lovercheck; Edward J. Hanson, Jr.

[57] ABSTRACT

One component, visible light-cured dental restorative compositions having fluoride release properties for the purpose of reducing the chances of secondary caries are provided. The compositions include inorganic particulate fluoride leachable glass.

29 Claims, 2 Drawing Sheets

RADIOPAQUE FLUORIDE RELEASING VLC DENTAL COMPOSITES AND THE USE OF SPECIFIC FILLERS THEREIN

This application is a continuation-in-part of U.S. Ser. No. 07/304,043, filed Jan. 30, 1989 now abandoned.

This invention relates to dental compositions which are curable by free radical polymerization and, preferably, by the action of visible light. More particularly, one-component dental composite formulations are disclosed which include a urethane-modified BisGMA and which maintain good color stability and exhibit superior properties relating to shrinkage, water serration, strength, depth of cure and packability characteristics when compared to prior art formulations. The dental compositions have fluoride release properties and are preferably radiopaque.

Composite or restorative materials should be distinguished from most unfilled dental compositions. Such unfilled dental materials comprise resins containing minor or no substantial amounts of filler materials. They are frequently used as sealants, glazes, bonding agents, or adhesives and may be used to coat a prepared tooth cavity prior to filling, thereby sealing off the tooth material against cracks and leaks adjacent to the filling. Such compositions have different viscosity requirements from dental restorative composite materials because low viscosities are needed. Certain restorative materials may be filled to an extent to allow reinforcement, yet retain sufficient flow so as to fill pits and fissures of teeth. Such "sealants" generally have less than or equal to 50% filler. By contrast, dental composite restorative materials used to replace lost tooth structure must have good forming characteristics so that they can be shaped to fit a cavity area or molded into place in order to repair chipped or damaged teeth. Furthermore, such restorative compositions must preferably be highly filled with inorganic materials in order to achieve satisfactory hardness and durability during service.

It will be appreciated by those skilled in the art that the use of one-component photoactivated materials is to be preferred over the more traditional thermochemical catalyst or redox activated systems because of the increased work time allowed by the use of photoinitiated polymerization. In a two-component catalyst or redox system, work time is determined by the reaction time once the two components are mixed. In a one-component photocured system, the practitioner may take whatever time is necessary for forming or molding the dental restoration into the tooth formation, and then effect extremely rapid curing by exposing the photocurable material to the appropriate wavelength of electromagnetic radiation.

There are prior art dental materials which utilize photoinitiators that are sensitive to visible light having wavelengths from about 4,000 angstroms to about 5,000 angstroms. These materials generally would be preferred over those materials which are cured with ultraviolet radiation because visible light is attenuated to a lesser degree by tooth structure than is ultraviolet radiation.

The present invention more specifically relates to the use of improved glass fillers in polymeric composites such as urethane resin based composites and a composite matrix made using said fillers and a method therefor. The composites of the invention have a cariostatic effect.

Ground glass fillers are used in restoratives to provide improved mechanical and physical properties in the restorative. Because fluoride has been shown to have beneficial properties with regard to preventing caries, it has been suggested that fluoride, in a leachable form, can be added to the ground glass to provide a continuing fluoride treatment to the tooth surfaces in contact or close proximity to the restorative. Such leachable fluoride generally is in the form of inorganic, water soluble fluorides. It has been found that such ground glasses, to which inorganic compounds such as sodium fluoride and strontium fluoride have been added, provide the expected fluoride treatment, but that the leaching of fluoride from these restoratives weakens the mechanical properties of the restorative.

It is known in the art that composites, such as urethane composites, are invisible to x-rays unless radiopaque fillers are added to the composite. It is desirable that radiopaque fillers have a density and a concentration in the composite such that the composite diffraction demonstrates x-ray absorption properties similar to or greater than those of natural teeth. Accordingly, the composites prepared according to the invention can be differentiated from dental caries and the like.

Accordingly, it is a principal object of this invention to provide compositions which are useful for dental applications.

It is a further object of this invention to provide a composite using a radiopaque glass filler material from which fluoride is leachable, but which will retain its physical integrity despite leaching of fluoride therefrom.

With regard to the resins used in the composite of the invention, it is to be understood that the term "bisphenol-A" is commonly used in the art to indicate the chemical compound 2,2-bis(4-hydroxyphenyl) propane. It is also to be understood that the term "Bis-GMA" is commonly used to indicate the chemical compound 2,2-bis[4-(2-hydroxy-3-methylacryloxypropoxy)-phenyl]-propane, otherwise referred to as "diglycidyl methacrylate of bisphenol A."

It is also to be understood that the term "ethoxylated bisphenol-A dimethacrylate" is commonly used in the art to indicate the chemical compound having the formula where n is a positive number, from 1 to about 5, and preferably from about 2 to about 3.

It is to be understood that NCO refers to an adduct of bis phenoxy- 1,2-hydroxy propane-1-methacrylate (also a name for BIS-GMA) and a mono or diisocyanate made according to Waller in U.S. Pat. No. 3,629,187, together with a diluent comprising triethyleneglycoldimethacrylate (TEGDMA).

It is also to be understood that the terms "acrylic" and "acrylate" are meant to include methacrylic and methacrylate.

PRIOR ART

Randlelev in U.S. Pat. No. 4,358,549 (Re 32,073) discloses dental filling compositions consisting essentially, in weight percent, of 45–65% $SiO_2$, 20–35% ZnO, 3–15% $B_2O_3$, about 0–19% $AlF_3$, 0–10% $Al_2O_3$, and 0–3% alkali metal oxides or alkaline earth metal oxides. No indication is given that fluoride can be leached from the glasses and the ZnO content is substantially greater than can be tolerated in the present inventive glasses.

Parkash et al. PCT publication No. WO 88/05652 disclose preparation of novel dental composites incorporating fluorosilicate glass fillers.

Kerr in European Patent Application A 0287213 (U.S. Pat. No. 4,746,686) discloses a visible light activated cavity liner.

Koblitz in European Patent Application A 0047097 discloses visible light curable dental compositions.

Danielson in European Patent Applicaton 0 380 796 discloses glasses exhibiting controlled fluoride release.

Shoji in French publication number 2,610,916 (U.S. Pat. No. 4,900,697) discloses fluoroaluminum silicates for cements.

Gaser et al. in European No. 0 238 025 (U.S. Pat. Nos. 4,767,798 and 4,882,365) discloses polymerization for dental use.

Waller in U.S. Pat. No. 4,746,686 discloses the development of visible light activated cavity liners for use in dental restoration. The liner provided a source of leachable calcium and fluoride and was comprised of a photopolymerizable matrix material, a photo initiator, a reducing agent, a synthetic hydroxyapatite filler, and a powdered glass ionomer filler. The single powdered glass composition provided consisted, in weight percent, of 31% $SiO_2$, 24% $A_2O_3$, 15% $AlPO_4$, 12% $AlF_3$, and 18% sodium aluminum fluoride. The glass described in the patent is a reactive, soluble glass, not suitable for use in a dental restorative.

R. L. Bowen and G. W. Cleek in "X-ray Opaque Reinforcing Fillers for Composite Materials, "*Journal of Dental Research*, January-February 1969, pages 79–82, discussed the preparation of glasses suitable for use as radiopaque fillers for dental restorative materials, those glasses being composed primarily of $Al_2O_3$, BaO, $BaF_2$, $B_2O_2$, and $SiO_2$. There was no reference to controllably leaching fluoride from the glasses and the compositions of the reported glasses, and none of the compositions described by Bowen et al anticipate or render obvious the compositions instantly claimed.

R. L. Bowen and G. W. Cleek in "A New Series of X-Ray-Opaque Reinforcing Fillers for Composite Materials," *Journal of Dental Research*. January-February 1972, pages 177–182, described a further series of glasses suitable for use as radiopaque fillers for dental restorative materials, those glasses being composed primarily of $Al_2O_3$, BaO, $B_2O_2$, and $SiO_2$, with various optional additives including $BaF_2$ and ZnO. Again, no mention is made of controllably leaching fluoride from the glasses; fluoride is merely an optional component and is absent from the preferred compositions. The glasses recited have compositions outside of the ranges required in the present inventive composites, and the reference appears to teach away from the use of monovalent anions in the composition for the purpose of providing a glass with a stable refractive index.

G. D. Derkson, P. J. Poon, and A. S. Richardson in "Fluoride Release from a Silicophosphate Cement with Added Fluoride, "*Journal of Dental Research*, 61, No. 5, pages 660–664, May 1982, disclosed increasing the rate of fluoride release from fluoride-containing cements used in dental cements and restorative materials. The authors added 10% by weight of $Na_2SiF_6$ to a commercial dental cement. Although leaching of fluoride from a dental cement is described, the thrust of the work was to increase the rate of fluoride release; there is no reference to providing compositions wherein the rate of, fluoride leaching would be relatively constant. Moreover, the present inventive glasses are most preferably substantially free from alkali metals, whereas the authors of the article purposefully added sodium ions.

M. L. Swartz, R. W. Phillips, and H. E. Clark in "Long-Term F Release from Glass Ionomer Cements," *Journal of Dental Research*, 63, No. 2, pages 158–160, February 1984, reported on experiments to study the rate of and the longevity of fluoride release from various silicate, silicophosphate, and fluoride-containing polycarboxylate, and glass ionomer filling and luting materials.

Although no glass composition data are furnished, these compositions are described as being glass ionomer type materials, are reactive and water soluble, and contain alkali metal salts preferably not included in the present inventive glasses.

Gasser et al, in U.S. Pat. No. 4,767,798 teaches a polymerizable, radiopaque dental compositions containing $YF_3$.

Kwan et al, in U.S. Pat. No. 4,772,325 teaches a dental composition containing a Lewis base and boron trifluoride.

Billington et al, in U.S. Pat. No. 4,797,431 and U.S. application 34,877, filed Apr. 6, 1987, describe processes for producing a radiopaque cement using strontium fluoride in the radiopacifying agent.

SUMMARY OF THE INVENTION

In accordance with the invention, the above and other objects and advantages are accomplished by providing stable, dental compositions which can be hardened by free radical polymerization, particularly by irradiation with visible light.

One component, visible light-cured dental restorative compositions having fluoride release properties for the purpose of reducing the chances of secondary caries are provided. The compositions include inorganic particulate fluoride leachable glass. In preferred embodiments the compositions of this invention comprise dental restorative materials which contain an inorganic, fluoride leachable and/or radiopaque, fluoride leachable glass, and an activated resin component.

As used herein, leachable is used to describe the tendency of fluoride ion to migrate from the glass when a composite or other composition incorporating the glass is contacted with an an aqueous environment such as saliva.

DETAILED DESCRIPTION OF THE INVENTION

The fluoride ion, because it chelates with and hardens the tooth surface, is beneficial in reducing or preventing the incidence of dental caries. Accordingly, it is believed that, in the treatment of dental caries, using a dental restorative having a leachable fluoride ion that can be released into the oral cavity over a sustained period of time, and incorporated and absorbed into the surrounding tooth structure is beneficial in reducing or eliminating the incidence of secondary caries.

In the illustrated embodiment, the composite may contain 1–20% by weight leachable fluoride, preferably 2–15% and most preferably 2–7%. The fluoride released from composite restoratives of the present invention is leached from within glass filler used in the restorative composition. The fluoride in the glass filler is an integral part of the glass matrix which is formed during melting of the glass. In contrast to the simple addition of inorganic fluoride (such as sodium or strontium fluoride, for example), to a composite the release of fluoride from the matrix of a glass filler is much more controlled and consistent and does not result in a deterioration of physical and mechanical properties of the composite due to removal of fluoride from the composite. Furthermore, the glass filler used in the composite of this invention can be silanated and thus bonded to the resin matrix to serve as a reinforcing media. This is not possible with conventional sources of fluoride.

In accordance with the invention is provided a dental composite restorative composition including a resin suitable for use in a dental restorative, and an inorganic filler comprising a non alkali, silantable, radiopaque glass containing extractable fluoride. The filler includes 14–8% $Al_2O_3$ and 25–35% BaO; 7–18% BaO and 7–18% SrO; or 4–7% ZnO.

FLUORIDE RELEASING GLASS

A composite made using the glasses described herein, used as a filler in a composite of the invention, upon exposure to an aqueous environment, releases fluoride ions at a relatively constant rate over a substantial period of time. Although fluoride ions are released from the composite there is essentially nc development of porosity or other physical breakdown effect of the composite. The glass filler is essentially free of alkali metal oxides and heavy toxic metals and consists essentially, expressed in terms of weight percent, of:

| $SiO_2$ | 40–56 | $B_2O_3$ | 5–12 |
|---|---|---|---|
| BaO | 15–35 | $F^-$ | 2–7 |
| $Al_2O_3$ | 4–12 | | |

The glasses used in the composite of this invention have been found to retain physical integrity even though caries preventing fluorides are leached from the glass. In an embodiment where the glass filler is silanated, the chemical integrity of the composite is improved, presumably because of chemical bonding between the filler and the composite resin material. Unexpectedly, it has been found that the composites of the invention have an improved translucency over composites made using other fluoride releasing agents such as NaF and $SrF_2$ as fillers for composite material, and accordingly aesthetically improved restorations are obtained.

RESIN

The resin component comprises one or more binder resins which include the reaction product of at least one vinyl ester of a polyglycidyl ether having secondary hydroxyl groups, and at least one isocyanate reactant. The isocyanate reacts with the vinyl ester through the secondary hydroxyl groups. Optionally, a second isocyanate reactant may be used which also reacts with the vinyl ester through the secondary hydroxyl groups. The second isocyanate reactant preferably is a diisocyanate compound.

The relative amounts of filler and resin components are selected in preferred embodiments such that the overall composition has a viscosity suitable for the particular dental application for which it is intended. Thus, the filler preferably includes from about 20 to about 90% by weight, based on the weight of the total composition. For dental restorative compositions, amounts of from about 50 to about 90% by weight, and more particularly, from about 70 to about 80% by weight are preferred.

The present dental compositions preferably comprise a unitary or one-component blend of binder resin(s), diluent monomer(s), filler(s) and photoactivating or photosensitizing system which is sensitive to visible light. Such compositions may optionally be modified through the addition of restorative modificants such as pigments, stabilizers, opacifiers, etc. These materials remain workable for a reasonable period of time in the dental operatory environment and are quickly hardened by exposure to visible light. At such time a rapid cure is effected to yield strong, durable, polishable dental restoratives having good color stability, strength, depth of cure, and water sorption properties.

GLASS COMPOSITIONS

The glass compositions of the present invention are prepared using barium fluoride as the primary source of leachable fluoride ion in the formed glass as described in U.S. Pat. No. 4,920,082 incorporated herein by reference in its entirety. Aluminum fluoride or other suitable fluoride, such as $ZnF_2$ or $SrF_2$, may be used as an additional source of fluoride ion.

Table I records a group of glasses illustrating the composition parameters. The oxide components are recited in terms of parts by weight, as calculated from the glass batch materials, and because it is not known with which cation(s) the fluoride is combined in the glass, it is merely reported in terms of F. The fluoride is reported in terms of its presence in the batch, i.e. F(B), and as analyzed in the glass prepared form the batch, i.e. F(A), thereby providing evidence of the relatively low loss of fluoride through volatilization during melting of the batch. Inasmuch as the sum of the individual ingredients closely approximates 100, for all practical purposes the values listed in Table I can be deemed to reflect weight percent.

The actual batch materials for the oxide constituents can comprise either the oxides, themselves, or other compounds which when melted together will be converted into the desired oxide in the proper proportion. For example, $BaCO_3$ may supply the source of BaO. Fluoride is conveniently introduced in the form of $BaF_2$ or $AlF_3$, the former constituting the preferred batch ingredient.

The batch ingredients are compounded, thoroughly tumble-mixed together to assist in securing a homogeneous melt, and then charged into platinum crucibles. After placing lids thereon, the crucibles are introduced into a furnace operating at about 1400° C., held therewithin for at least four (4) hours, depending upon the weight of the batch, to achieve good melting. Thus, longer furnace times are required with large batches to assure homogeneous melts. Thereafter, the crucibles are removed from the furnace and the melts poured as a relatively fine stream into a bath of cold tap water. This practice, termed drigaging, breaks up the glass stream into small particles which can be readily milled or otherwise comminuted to very small dimensions. The drigaged samples are reduced to powders having an average diameter of about 5-microns by ballmilling in $Al_2O_3$ containers with $Al_2O_3$ milling media.

A screening test is used to provide an estimate of the amount of fluoride leached from the inventive glasses. This test involves immersing 1 gram samples of powdered glass into 100 ml distilled water for 25 hours at room temperature and analyzing the resulting solution for fluoride, the concentration present therein being reported in terms of micrograms/ml. The results of that testing are recorded in the following tables as the release of fluoride, i.e., F(R).

TABLE 1

|  | 1 | 2 | 3 | 4 | 5 | 6 | 7 |
|---|---|---|---|---|---|---|---|
| $SiO_2$ | 49.0 | 47.4 | 48.7 | 46.9 | 47.2 | 44.1 | 47.4 |
| $Al_2O_3$ | 8.3 | 8.0 | 8.3 | 8.0 | 8.1 | 7.5 | 8.0 |
| $B_2O_3$ | 8.4 | 8.3 | 8.3 | 8.0 | 8.1 | 7.5 | 8.1 |
| BaO | 30.3 | 29.3 | 30.1 | 29.0 | 29.2 | 27.2 | 29.3 |
| SrO* | 0.3 | — | 0.5 | 0.5 | 0.3 | — | — |
| F(B) | 3.6 | 7.1 | 3.9 | 7.6 | 7.3 | 13.7 | 7.1 |
| F(A) | 3.1 | 4.6 | 3.6 | 4.6 | 4.5 | 5,4 | — |
| F(R) | 3.4 | 6.0 | 3.2 | 6.6 | 7.0 | 9.0 | 3.1 |

|  | 8 | 9 | 10 | 11 | 12 | 13 | 14 |
|---|---|---|---|---|---|---|---|
| $SiO_2$ | 46.4 | 45.4 | 43.4 | 45.4 | 45.4 | 43.3 | 41.4 |
| $Al_2O_3$ | 8.0 | 8.0 | 8.0 | 8.0 | 8.0 | 8.0 | 8.0 |
| $B_2O_3$ | 8.1 | 8.1 | 8.1 | 8.1 | 8.1 | 8.1 | 8.1 |
| BaO | 29.3 | 29.3 | 29.3 | 29.3 | 29.3 | 29.3 | 29.3 |
| F(B) | 7.1 | 7.1 | 7.1 | 7.1 | 7.1 | 7.1 | 7.1 |
| F(A) |  |  |  |  |  |  |  |
| $P_2O_5$ | 1.0 | 2.0 | 4.0 | — | — | 2.0 | 4.0 |
| ZnO | — | — | — | 2.0 | — | 2.0 | 2.0 |
| $SnO_2$ | — | — | — | — | 2.0 | — | — |
| F(R) | 4.5 | 4.5 | 3.7 | 3.0 | 3.0 | 3.2 | 2.6 |

*SrO was contaminant in the BaO batch material

Table II recites a second group of glasses, the compositions of which are reported in like manner to those in Table I. In each batch the fluoride component is introduced in the form of $BaF_2$, the amount of that component being recorded in the Table. Table II also lists the total BaO concentration, i.e., BaO(T), as calculated from the batch materials, along with the batched fluoride, as calculated from the $BaF_2$, and the fluoride as analyzed in the glass. The batch materials were compounded, mixed, melted, drigaged and powdered in like manner to the procedure described above with respect to the glasses reported in Table I. Fluoride release in the above-described aqueous solution test is also recorded.

TABLE II

|  | 15 | 16 | 17 | 18 | 19 |
|---|---|---|---|---|---|
| $SiO_2$ | 49.1 | 51.7 | 45.9 | 49.3 | 43.6 |
| $Al_2O_3$ | 8.3 | 11.0 | 10.5 | 10.8 | 10.3 |
| $B_2O_3$ | 8.4 | 6.8 | 6.5 | 10.1 | 9.6 |
| BaO | 4.3 | — | 8.3 | — | 8.2 |
| $BaF_2$ | 29.9 | 30.5 | 28.9 | 29.9 | 28.4 |
| BaO(T) | 30.4 | 26.6 | 33.6 | 26.1 | 33.0 |
| F(B) | 6.5 | 6.6 | 6.3 | 6.5 | 6.2 |
| F(A) | 5.4 | 5.0 | 6.0 | 5.3 | 5.7 |

TABLE II-continued

| F(R) | 4.2 | 2.3 | 2.9 | 1.3 | 1.6 |
|---|---|---|---|---|---|
|  | 20 | 21 | 22 | 23 |  |
| $SiO_2$ | 55.9 | 49.7 | 53.3 | 47.3 |  |
| $Al_2O_3$ | 6.1 | 5.8 | 6.0 | 5.7 |  |
| $B_2O_1$ | 7.0 | 6.6 | 10.3 | 9.8 |  |
| BaO | — | 8.5 | — | 8.3 |  |
| $BaF_2$ | 31.1 | 29.5 | 30.5 | 28.9 |  |
| BaO(T) | 27.2 | 34.3 | 26.7 | 33.6 |  |
| F(B) | 6.7 | 6.4 | 6.6 | 6.3 |  |
| F(A) | 5.0 | 5.7 | 4.6 | 5.3 |  |
| F(R) | 10.7 | 17.0 | 10.5 | 20.8 |  |

Table III records a series of glass compositions wherein SrO replaced BaO in stepwise fashion. The fluoride content is tabulated in terms of weight percent as calculated form the batch materials and as analyzed in the glass. Table IIIA recites the proportions of BaO and SrO in terms of mole percent. Again, the batches are compounded, mixed, melted, drigaged, and powdered in like manner to the compositions reported in Table I. Fluoride release in the above-described aqueous solution test is also reported.

The glasses of Table III also illustrate the increase in phase separation occurring in the glass when SrO is substituted for BaO, as estimated by visual observation of the glass at room temperature. Thus, an annealed slab of solely BaO-containing glass appears translucent or very weakly opaque to the eye. Upon replacement with SrO, the glass develops greater opacity until, upon complete substitution, the glass is totally opaque. Finally, Table III lists measurement of phase separated droplet sizes observed in transmission electron micrographs (TEM) of fractured glass surfaces.

TABLE III

|  | 24 | 25 | 26 | 27 | 28 |
|---|---|---|---|---|---|
| $SiO_2$ | 47.1 | 47.9 | 48.8 | 50.0 | 42.0 |
| $Al_2O_3$ | 7.9 | 8.0 | 8.2 | 8.4 | 8.7 |
| $B_2O_3$ | 8.1 | 8.2 | 8.4 | 8.6 | 8.9 |
| BaO | 29.6 | 24.7 | 19.5 | 12.4 | — |
| SrO | — | 3.7 | 7.5 | 12.9 | 12.1 |
| F(B) | 7.3 | 7.4 | 7.5 | 7.6 | 7.9 |
| F(A) | 5.4 | 5.3 | 5.6 | 5.7 | 5.8 |
| F(R) | 3.0 | 6.1 | 6.2 | 5.6 | 5.2 |
| Opacity | Weak | Weak | Medium | Medium | Opaque |
| TEM | 500-1400A | — | 800-2000A | — | 2000A |

TABLE IIIA

|  | 24 | 25 | 26 | 27 | 28 |
|---|---|---|---|---|---|
| BaO | 16.5 | 13.5 | 10.5 | 6.5 | — |
| SrO | — | 3.0 | 6.0 | 10.0 | 16.5 |

Table IV lists a number of glass compositions wherein $ZnF_2$ is substituted for $BaF_2$ in stepwise fashion. The batched fluoride is calculated from $ZnF_2$ and $BaF_2$. The analyzed fluoride is also reported. Table IVA records the proportions of $ZnF_2$ and $BaF_2$ in terms of mole percent. Yet again the batches are compounded, mixed, melted, drigaged and powdered in like manner to the compositions reported in Table I.

TABLE IV

|  | 29 | 30 | 31 | 32 | 33 |
|---|---|---|---|---|---|
| $SiO_2$ | 48.6 | 50.3 | 52.2 | 54.2 | 56.7 |
| $Al_2O_3$ | 8.1 | 8.4 | 8.7 | 9.1 | 9.5 |
| $B_2O_3$ | 8.4 | 8.7 | 9.0 | 9.3 | 9.8 |
| $BaF_2$ | 54.9 | 27.4 | 19.3 | 10.6 | — |
| $ZnF_2$ | — | 5.2 | 10.7 | 16.7 | 24.1 |

TABLE IV-continued

| | | | | | |
|---|---|---|---|---|---|
| F(B) | 7.3 | 7.6 | 7.9 | 8.2 | 8.5 |
| F(A) | 5.6 | 5.2 | 4.4 | 3.0 | 1.27 |

| | 34 | 35 | 36 | 37 |
|---|---|---|---|---|
| SiO$_2$ | 46.7 | 49.3 | 52.2 | 55.4 |
| Al$_2$O$_3$ | 5.6 | 5.9 | 6.2 | 6.6 |
| B$_2$O$_3$ | 9.7 | 10.3 | 10.9 | 11.5 |
| BaF$_2$ | 37.9 | 26.8 | 14.0 | — |
| ZnF$_2$ | — | 7.8 | 16.7 | 26.5 |
| F(B) | 7.9 | 8.3 | 8.8 | 9.4 |
| F(A) | 5.4 | 4.4 | 3.0 | 1.25 |

TABLE IVA

| | 29 | 30 | 31 | 32 | 33 | 34 | 35 | 36 | 37 |
|---|---|---|---|---|---|---|---|---|---|
| BaF$_2$ | 16.5 | 12.5 | 8.5 | 4.5 | — | 18.2 | 12.2 | 6.0 | — |
| ZnF$_2$ | — | 4.0 | 8.0 | 12.0 | 16.5 | — | 6.0 | 12.2 | 18.2 |

In order to assess in influences of batch materials and melting times and temperatures upon fluoride retention in the glass, the six glass compositions recorded in Table V are examined. Thus, comparisons are made between the use of BaF$_2$ and AlF$_3$ as sources of fluoride while varying the times (2, 3 and 4 hours) and temperatures (1300° C. and 1400° C.) of melting. The concentrations of fluoride in the batch, i.e., F(B) as calculated from BaF$_2$ and AlF$_3$, and the analyzed values of fluoride in the glass, i.e., F(A), are recited.

TABLE V

| | 38 | 39 | 40 | 41 | 42 | 43 |
|---|---|---|---|---|---|---|
| SiO$_2$ | 47.4 | 47.4 | 47.4 | 46.9 | 46.9 | 46.9 |
| Al$_2$O$_3$ | 8.0 | 8.0 | 8.0 | — | — | — |
| B$_2$O$_3$ | 8.1 | 8.1 | 8.1 | 8.0 | 8.0 | 8.0 |
| BaF$_2$ | 33.6 | 33.6 | 33.6 | — | — | — |
| BaO | — | — | — | 29.0 | 29.0 | 29.0 |
| AlF$_3$ | — | — | — | 13.6 | 13.6 | 13.6 |
| F(B) | 7.1 | 7.1 | 7.1 | 7.6 | 7.6 | 7.6 |
| 1300° C. | 2 hrs | 3 hrs | 4 hrs | 2 hrs | 3 hrs | 4 hrs |
| F(A) | 5.7 | 5.5 | 5.5 | 5.5 | 5.4 | 5.4 |
| 1400° C. | 2 hrs | 3 hrs | 4 hrs | 2 hrs | 3 hrs | 4 hrs |
| F(A) | 5.4 | 5.3 | 5.2 | 5.2 | 5.1 | 5.1 |

In order to investigate the effect upon fluoride release from the inventive glasses when exposed to a subsequent heat treatment, the milled, drigaged powders of Examples 1–6 are heated to 740° C. and maintained at the temperature of 45 minutes. A comparison of the fluoride release in the base powders, i.e., F(R), with the fluoride release in the heat treated powders, i.e., F(HT), is reported in Table VI.

TABLE VI

| | 1 | 2 | 3 | 4 | 5 | 6 |
|---|---|---|---|---|---|---|
| F(R) | 3.4 | 6.0 | 3.2 | 6.6 | 7.0 | 9.0 |
| F(HT) | 3.0 | 14.0 | 6.0 | 13.0 | 13.0 | 5.0 |

A study of the above Tables points up several features with respect to volatilization of fluorine during melting of the batch and the release of fluoride from the glasses when exposed to aqueous solutions.

First, the total fluoride that can be retained in the glass is about 7% by weight;

Second, batch levels of fluoride in excess of about 8% by weight are ineffective in promoting increased fluoride retention, inasmuch as much higher levels appear to result in greater volatilization of fluorine, with no additional fluoride being retained in the glass;

Third, the substitution of Zn for Ba dramatically increases the rate and amount of fluorine volatilization;

Fourth, volatilization of fluorine appears to take place relatively early in the melting process; that is, very little decrease in fluoride retained in the glass is seen after two hours;

Fifth, higher melting temperatures foster greater volatilization of fluorine;

Sixth, whereas higher levels of fluoride can be batched with AlF$_3$ and ZnF$_2$, volatilization of fluorine during melting of the batch is considerably less when BaF$_2$ comprises the fluoride-containing batch ingredient; that is, higher BaO contents appear to aid in fluorine retention;

Seventh, in general, higher levels of fluoride in the glass lead to greater sustained release of fluoride when the glass is contacted with an aqueous solution;

Eighth, in general, glasses of lower Al$_2$O$_3$ content will demonstrate greater release of fluoride when immersed in an aqueous solution, as will glasses of higher BaO concentrations;

Ninth, in general, additional heat treatment of the inventive glasses does not seriously impact the release of fluoride therefrom this lack of substantial effect has been conjectured as being derived from the fact that the glasses are phase separated, the resulting microstructure being relatively immune to the effects of heat treatment; and Tenth, the presence of phase separation is observed in the glasses useful in accordance with the inventor; the presence thereof greatly increasing when SrO is substituted for BaO.

To illustrate the long term fluoride release capability of the glasses useful in accordance with the invention, several of the glasses reported in Tables I, II, and III are subjected to a Soxhlet Extraction utilizing distilled water as the extractant. The amount of fluoride in the aqueous extraction solution is analyzed daily in terms of parts per million (ppm) over a period of seven days. Because of the high temperatures necessarily involved in Soxhlet Extractions, the use thereof here constitutes a very accelerated test of fluoride release in water, when compared with exposure to water under normal ambient conditions. Nevertheless, the procedure does provide a rational estimate as to the behavior of a glass under less severe temperature conditions.

In the following tests recorded in Table VII, 10 gram samples of the powdered glasses are used and the fluoride release measure employing a fluoride ion selective electrode with four point calibration, viz, 1, 10, 25 and 100 ppm standards.

TABLE VII

| | 2 | 3 | 4 | 5 | 6 |
|---|---|---|---|---|---|
| Day 1 | 27018 | 201160 | 17616 | 16002 | 42769 |
| Day 2 | 9804 | 195870 | 13188 | 13497 | 20923 |
| Day 3 | 6045 | 49629 | 9491 | 9529 | 14107 |
| Day 4 | 5232 | 45051 | 9409 | 9224 | 14274 |
| Day 5 | 5740 | 40607 | 9136 | 9174 | 14272 |
| Day 6 | 6516 | 29317 | 7356 | 9008 | 11655 |
| Day 7 | 4303 | 17996 | 5870 | 6480 | 7355 |

As is readily apparent from Table VII, after an initial substantial release of fluoride the glasses useful in accordance with the invention settle to a release level of about 25% of that of the original release, and that level is maintained for several days thereafter.

In contrast, an alkali metal-, alkaline earth metal-containing aluminoborofluorosilicate opal glass of the type described in U.S. Pat. No. 4,080,215 and marketed by Corning Glass Works, Corning, N.Y., under Code 6005 having an analyzed fluoride content of about 5%, when subjected to Soxhlet Extraction, exhibited the following release of fluoride, in parts per million:

Day 1: 130
Day 2: 2.9
Day 3: 2.2
Day 4: 2.3
Day 5: 2.3
Day 6: 2.3
Day 7: 2.3

It is immediately evident that, after the initial release of fluoride, the glass becomes quite resistant to attack by water, the release of fluoride becoming virtually inconsequential. It is conjectured that the initial large extraction of fluoride results from alkali metal fluoride being leached out of the glass. The remaining small amount of fluoride is rather tightly bonded to the other glass components.

With regard to $ZnF_2$, experience has demonstrated that the inclusion of substantial amounts of ZnO (Zn is analyzed in the completed glass as ZnO content) in the glass composition leads to significant increases in fluorine volatilization during melting of the batch. Consequently, substitutions of ZnO for BaO (the presence of Ba in the completed glass in measured as BaO content) in the glass will customarily be limited to no more than about one-third on a molar basis and, preferably, no more than 7% by weight ZnO based on the total weight of the glass.

Minor amounts of extraneous additions, such as $SnO_2$ and $P_2O_5$, may be present in the melt at levels not exceeding about 5% by weight total without adversely affecting the leaching character of the glass. Alkali metal oxides, however, will preferably be absent, because they reduce the overall chemical durability of the glass and cause the rapid leaching of fluoride.

The glass fillers described herein, used in a composite restorative material are hydrolytically stable, as compared to prior art fillers that use sodium fluoride and/or strontium fluoride as a fluoride ion source. Although fluoride ion is leached from the composite, the composite maintains physical integrity over a much longer period of time as compared to composites produced using prior art fluoride fillers.

COMPOSITES FORMED FROM POLYMERIZABLE BLENDS

Surprisingly, it has been found that the composite restoratives of the present invention have improved translucency as compared to composites which include NaF, and retains its aesthetic appearance over a longer period of time as demonstrated in accelerated aging tests. The compositions of this invention comprise free radical polymerizable, hardenable blends comprising binder resin(s), diluent monomer(s), and a free radical polymerization system. In its more preferred form, the invention relates to dental composite materials which comprise visible light polymerizable, hardenable blends comprising filler(s), binder resin(s), diluent monomer(s), and a visible light photosensitizing system. Such blends may optionally include pigments, opacifiers, stabilizers, handling agents and other modificants as will be appreciated by those skilled in the art.

The binder resins suitable for use in the practice of one or more embodiments of this invention include the reaction products of a vinyl ester of a polyglycidyl ether having secondary hydroxyl groups and at least one isocyanate reacted through those hydroxyl groups. Optionally, the isocyanate used may be ethylenically unsaturated and reaction products of such unsaturated reactants are described in detail in U.S. Pat. No. 4,383,091 to Burton, incorporated herein by reference.

In addition to the foregoing reaction products of vinyl esters and isocyanates, including ethylenically unsaturated isocyanates, suitable binder resins include those prepared by reacting the vinyl esters through the secondary hydroxyl groups with a mixture of isocyanate reactants, wherein one of the isocyanate reactants may contain ethylenic unsaturation. The isocyanate reactant may comprise saturated or unsaturated, substituted or unsubstituted, aliphatic, aromatic or cycloaliphatic mono-or diisocyanate compounds. Examples of such isocyanate compounds include trimethylhexamethylene diisocyanate, hexamethylene diisocyanate, phenylene diisocyanate or the like as described in the prior art mentioned above.

For use herein, the vinyl ester resin can be prepared from any glycidyl polyether. Useful glycidyl ethers are those of polyhydric alcohols and phenols. Such glycidyl polyethers are commercially available or are readily prepared by reacting at least two moles of an epihalohydrin or glycerol dihalohydrin with one mole of the polyhydric alcohol or phenol together with a sufficient amount of caustic to react with the halogen of the halohydrin. The products are characterized by the presence of more than one glycidyl ether group per molecule.

The useful acids for making the vinyl ester resins are those ethylenically unsaturated monocarboxylic acids such as acrylic, methacrylic, cinnamic acids and their halogenated isomers. Also included are the hydroxyalkyl acrylate or methacrylate half esters of dicarboxylic acids as described in U.S. Pat. No. 3,367,992 to Bearden wherein the hydroxyalkyl group preferably contains from 2 to 6 carbon atoms.

The glycidyl ether and the acid are reacted in about stoichiometric equivalency, generally with heating in the presence of a catalyst, such as a trivalent chromium salt, as, for example, chromium trichloride. In a preferred embodiment, the above reaction can be exemplified by the following reaction between the glycidyl ether of bisphenol-A and methacrylic acid:

It is commonplace in the vinyl ester resin art to adjust the viscosity of the liquid uncured resin with a reactive diluent, usually a copolymerizable monomer. Suitable monomers for this use include alkyl methacrylates, alkylene dimethacrylates, trimethacrylates, and higher methacrylates, alkyl acrylates, alkylene diacrylates, triacrylates and higher acrylates. Examples of suitable diluent monomers include triethyleneglycol dimethacrylate, 1,6-hexanediol dimethacrylate, ethoxylated bisphenol-A dimethacrylate, 1,3-buty-lenedimethacrylate, trimethylol propane trimethacrylate, and the like.

The diluent monomer(s) are added to the compositions of this invention in an amount sufficient to result in polymerizable resin components having a viscosity between about 1,500 and about 300,000 centipoises at 25° C. For the preferred dental restorative materials, the reactive diluents are added in an amount sufficient to result in polymerizable viscosity between about 2,500 and about 150,000 and preferably between about 6,000 and about 75,000 centipoises at 25° C.

The photosensitizing system employed in the formulation of dental materials according to the preferred practice of this invention comprises two components, an alpha diketone photosensitive species (also known as an alpha, beta diketone) and an amine reducing agent. While any alpha diketone, or other known photoinitiator which is capable of initiating polymerization in the polymerizable systems of this invention may be employed, camphorquinone, benzil, biacetyl, 9, 10-phenanthrenequinone, and naphthoquinone have been found to be preferred. Non-aromatic alpha diketones, especially camphorquinone and biacetyl have been found to be the best photoinitiators for use in the practice of this invention. Such non-aromatic species are believed to be most useful in formulating restoratives which pass the A.D.A. color stability test. Most preferred is camphorquinone.

The alpha diketone is combined with an amine reducing agent; the two taken together form the visible light sensitizing system useful for the practice of this invention. Numerous amines have been found to be useful as reducing agents for the alpha diketones used herein. Thus, amines such as tributylamine and tripropylamine are useful. Still other useful amines are substituted tertiary amines, such as N-alkyldialkanolamines trialkanolamines, and substituted aromatic amines. Those skilled in the art will appreciate that numerous other alpha diketones and amine reducing agents may be employed without deviating from the spirit of this invention.

The amount of alpha diketone photosensitizer is controlled to comprise from about 0.01 to about 1% by weight based upon the total weight of the binder resin, diluent monomer and photosensitizing system. It is even more preferred to employ from about 0.05 to about 0.5% by weight of alpha diketone and to use non-aromatic species such as camphorquinone or biacetyl. The amount of amine reducing agent is less critical. It is useful to employ from about 0.1 to about 5% of amine, with from about 0.3 to about 1% being preferred, based on the total weight of binder, diluent and photosensitizing system. The photosensitizing system may also include stabilizers and other modificants. For example, it may be desirable to include a small amount of BHT. Similarly, a small amount of 2-hydroxy-4-methoxybenzophenone may be added to enhance color stability under ultraviolet radiation, and a small amount of 2,5-dihydroxy diethylterephthalate may be added to increase the fluorescence of the composite to more closely match natural teeth.

For the formulation of the visible light polymerizable compositions of this invention for use as a restorative composite, besides the fluoride leachable glass fillers described above, the binder resin, diluent and visible light photosensitizing system may be blended together with other leachable fluoride fillers and, optionally, other non-fluoride leachable fillers, as well as pigments and modificants. The fluoride fillers (preferably in very small amounts) may be used if an initial burst of fluoride from the restorative is desired. Those skilled in the art will appreciate that the relative amount of leachable fluoride and non-fluoride fillers loading which may be accomplished with a given resinous system will depend upon several variables including the identity of the resins, the identity and the particle sizes of the fillers, and the desired end use of the composition. It must be appreciated that, for a given resin formulation, judicious choice of filler type and filler particle size must be made. The filler blends must be such that the transmittance of visible light by the preferred restorative compositions is sufficient for polymerization to take place. Those skilled in the art will be able to select appropriate filler blends and to determine filler particles sizes based upon this requirement.

Among those fillers which are especially suited for use in the practice of this invention are inorganic glasses. Preferred among these are barium aluminum glasses. Preferred among these are barium aluminum borosilicate, lithium aluminum borosilicate, strontium, lanthanum, tantalum, etc., glasses and related materials. Silica, especially in submicron sizes, quartz, and other fillers may also be employed in some formulations. Such fillers are preferably silanated prior to use in the preferred restoratives of this invention. Silanation is well known to those skilled in the art.

It is known that smaller sized filler particles result in highly polishable dental materials, but that the concomitant increase in surface area diminishes the overall filler loading possible with a given resin. Such lower loadings may be manifested by lesser degrees of strength, hardness, and durability in the resulting polymerized structures. It is possible, however, and beneficial in some cases, to employ submicron sized fillers in combination with a mixture of larger sized fillers. In general, weight ratios of from about 10:90 to about 90:10 filler to resin may be used, with from about 50:50 to about 85:15 filler to resin being preferred, and from about 70:30 to about 80:20 filler to resin being even more preferred.

In an embodiment where the composite will be used as a posterior restorative, the formulations of visible light curable compositions of this invention may contain a blend of glass and silicon fillers. For example a blend comprising 35–60 weight % of silanated milled barium glass (mean particle size of 5–9 microns), and more preferably 25–50 weight % of silanated milled barium glass (mean particle size of 2–5 microns), and 5–15 weight % of silanated "Aerosil OX-50" submicron fumed silica (sold by Degussa) may be used.

Those skilled in the art will recognize that the exact composition of the composite material may be adjusted to provide specific properties for a particular use.

When using a resin of the present invention with reduced amounts of fillers, such compositions are useful for example as cements, sealants, bonding agents and the like.

Pigments, opacifiers, brightening agents, handling agents and other modificants may be included in the compositions of this invention without departing from its spirit.

While the various components of the present formulations may be added in any order, it has been found useful and convenient to first form the activated resin component by mixing the binder resin(s) and diluent(s) together, and then adding the photosensitizing system components. Thereafter, the filler(s) together with pigments and other modifying agents may be blended with the activated resin component to complete the formulations. In practice, the binder resin and diluent are mixed together in a proportion such that the final polymerizable composition will have a viscosity suitable for dental applications such as the filling of teeth.

The methods of use of the visible light curable compositions of this invention follow, to an extent, those currently practiced by those skilled in the art. Thus, the surface to be repaired is cleansed of decayed material and acid etched to promote bonding. At this point, a bonding agent may be employed by coating it upon the surface to be repaired. A material according to this invention is then molded into place in the conventional fashion. At this point, visible light is directed onto the restorative materials by any suitable source. One such source is described in the application of Gonser "Visible Light Apparatus for Curing Photocurable Compositions", assigned to the Assignee of this invention and accorded Ser. No. 182,643, filed Aug. 29, 1980, now U.S. Pat. No. 4,385,344.

This exposure may take place directly or through one or more surfaces of tooth material due to the significant transmittance of tooth material to visible light. Following exposure, the restorative material undergoes polymerization. During this process, and afterward, the materials of this invention exhibit color stability in accordance with A.D.A. Specification Number 27.

During screening of various glass compositions having fluoride as part of their matrix, two glass compositions identified as WP and XT (as described in Examples 7 and 8 below) were selected, with XT being preferred. The fluoride release from selected compositions (i.e. composites, sealants, cements, etc.) using these glasses as reinforcing fillers was evaluated in what is referred to as the "static" method. This procedure prepares a disc of material (20×1 mm) that is immersed in deionized water and fluoride released into the water is measured periodically.

As a screening process, various PRISMA-FIL® type compositions, (PRISMA-FIL is a product of L. D. Caulk, a Division of Dentsply International Inc.) were prepared where the fluoride glass was used as filler in place of currently used fillers. Testing showed that the XT glass clearly releases more fluoride over the measured period than the WP glass.

Figure 1:
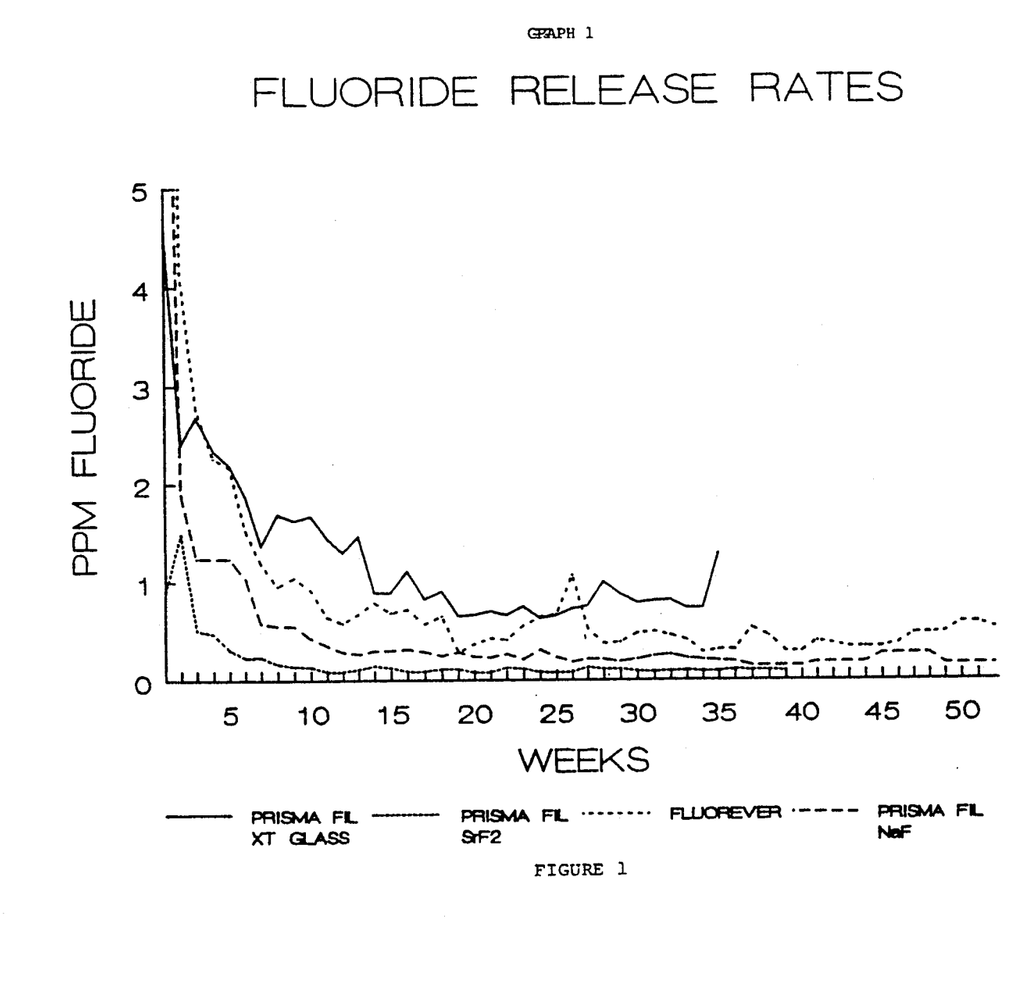
FIG. 1 (Graph 1) is a schematic representation of fluoride release rates in accordance with the invention.

Graph 1 shows the ppm of fluoride released from a restorative having fluoride releasing glass filler after placing it in contact with the aqueous medium. Preferably the glass filler in the restorative is adapted to release fluoride through leaching into an aqueous medium at a rate sufficient to maintain from about 0.5 to about 2.0 ppm of fluoride in the medium over the twenty week period between 10 and 30 weeks from first placing the restorative in contact with the aqueous medium. More preferably the glass filler in the restorative is adapted to release fluoride through leaching into an aqueous medium at a rate sufficient to maintain from about 0.5 to about 3.0 ppm of fluoride in the medium over the thirty week period between 5 and 35 weeks from first placing the restorative in contact with the aqueous medium.

The concept of the invention will be more apparent from the following illustrative examples wherein all parts and percentages are by weight, unless otherwise indicated.

EXAMPLE 1—Preparation of Ethoxylated Bisphenol-A Dimethacrylate (EBPADMA) Urethane Resin An 18 liter resin kettle equipped with a stirrer and dry air bleed was charged with 2,2-Bis[4-(2-hydroxy-3-methacryoxypropoxy)phenyl]propane (Bis-GMA) (4,918g, 9.6 moles), ethoxylated bisphenol-A (5,340g, 11.8 moles), triethyleneglycol dimethacrylate (TEGDMA) (3,993g, 13.7 moles), and dibutyltin dilaurate (DBTDL) (56g, 0.08 mole). With efficient stirring, hexamethylene diisocyanate (HMDI) (1,346g, 7.3 moles), dissolved in triethylene glycol dimethacrylate (1,346g, 4.8 moles), was added dropwise to the resin kettle. The resin temperature was maintained at or below 50° C., and the addition was complete in about one and one-half hours. The resin was stirred for about sixteen hours while the resin temperature was maintained below 50° C. Residual isocyanate, as determined by infrared analysis, was less than 0.01 percent.

The weight % of the various constituents used to prepare the EBPADMA urethane resin is as follows:

| | |
|---|---|
| Bis-GMA[1] | 28.93% |
| EBPADMA[2] | 31.41% |
| TEGDMA[3] | 31.41% |
| Dibutyl tin dilaureate (DBTDL) | 0.33% |
| Hexamethylene diisocyanate (HMDI) | 7.92% |
| | 100.00% |

[1]2,2-Bis[4-(2-hydroxy-3-methacryloxyproxy)phenyl] propane
[2]Ethoxylated bis-phenol A dimethacrylate
[3]Triethylene glycol dimethacrylate Theoretically, approximately 76% of the pendant hydroxy functions of Bis-GMA are reacted with HMDI to yield a urethane modified Bis-GMA prepolymer. EBPADMA is utilized both as base and diluent monomer. TEGDMA is a diluent monomer for additional viscosity control. DBTDL is the urethane catalyst. The resultant resin viscosity is approximately 6,000–16,000 cps at 25° C.

EXAMPLE 2—Resin Activation of EBPADMA Resin

| | % |
|---|---|
| EBPADMA Urethane Resin | 98.582 |
| BHT[1] | 0.025 |
| CQ[2] | 0.163 |
| Flublau L229[3] conc. (10% in NCO) | 0.180 |
| Uvinul M-40[4] | 0.400 |
| MDEA[5] | 0.650 |
| | 100.000 |

[1]2,6-Di-tert-butyl-4-methylphenol
[2]Camphorquinone
[3]2,5-Dihydroxy diethylterephthalate
[4]2-Hydroxy-4-methoxybenzophenone (UV absorber)
[5]Methyl diethanolamine All apparatus used was clean and dry. All procedures involving the activated resin were carried out under amber illumination.

All ingredients were dissolved utilizing the DISPERSATOR as energy source. Agitation times were about one (1) hour.

The activated resin was held for the composite preparation. Prolonged storage of activated resin in bulk was avoided.

EXAMPLE 13—Powder Blend for EBPADMA Composite

| | % |
|---|---|
| Silanated Barium Silicate glass (SBBAS) | 98.276 |
| Iron oxide yellow conc.* (10% dispersed on SBBAS) | 0.035 |
| Iron oxide red conc. (1% dispersed on SBBAS) | 0.009 |
| Black pigment conc. (0.07% dispersed on SBBAS) | 0.080 |
| Titanium dioxide conc. (10% dispersed on SBBAS) | 0.300 |
| Aerosil R-972 (fumed silica) | 1.300 |
| | 100.00 |

*Concentrates made herein were made by tumbling the colors on the glass support for ¼ hour on slow rollers and then sieved through #8 silk.

All apparatus used was clean and dry.

All pigment concentrates (conc.) were weighed on an analytical balance.

The powder blends were tumbled on rollers for fifteen (15) minutes followed by two (2) passes through a #8 silk.

The barium glass was milled to have a narrow particle size distribution around an approximate 1.5 micron mean. Optical microscopic and COULTER counter analysis of the milled particles indicate an upper size limit of approximately 3-5 microns.

EXAMPLE 4—EBPADMA Composite

| Composite Ratios | |
|---|---|
| | % |
| Activated Resin | 22.50 |
| Powder Blend | 77.50 |
| | 100.00 |

All apparatus used was clean and dry.

All procedures involving the activated resin or pastes were carried out under amber illumination.

Pastes were blended with 77.5% powder and 22.5% resin or at a powder/resin ratio of 3.44/1.

| Physical Properties | | |
|---|---|---|
| | FUL-FIL ® | EXAMPLE 4 |
| Filler Weight, % | 77 | 77.5 |
| Cure Depth, mm @ 10 seconds | 5.0 | 3.5 |
| Diametral Tensile, 24 hour, MPa | 54 | 60 |
| Compressive Strength, 24 hour, MPa | 295 | 345 |
| Transverse Strength, 24 hour, MPa | 110 | 119 |
| Flexural Modulus, 24 hour, MPa | 7500 | 7350 |
| Water Sorption, 7 days, mg/cm2 | 0.7 | 0.5 |
| Color Stability, 24 hour UV | Pass* | Pass* |
| Color Stability, 7 days wet @ 50° C. | Pass* | Pass* |
| Packability, g/mm$^2$ | 175 | 225 |
| Mean Filler particle Size in Microns | 2-4[1] | 1.5[2] |

*Color change perceptible with difficulty with reference to procedures accepted by ADA spec 27.
[1](maximum particle size about 15 um).
[2](maximum particle size about 5 um).

Water sorption was reduced approximately 25% versus FUL-FIL by resin modifications. The resultant composite finishes to a reflective smooth surface that is superior to other small-particle composites. The smooth surface enhances esthetics and is believed to improve long-term wear and stain resistance. The composition is sufficiently dense for handling anterior and posterior applications.

METHOD OF FLUORIDE RELEASE MEASUREMENT

Typically, the ratio of composite material to water is about 1:10 in a static method of fluoride release measurement.

EXAMPLE 5—Static Method

A chip of composite material of Example 4, 1 mm thick and having a 20 mm diameter was prepared by curing the composite under a General Electric photoflood lamp (EBV No.2) with a mylar cover for two minutes. A tiny hole was drilled in the chip. The specimen was tied with a nylon thread, suspended in 10 ml deionized water in a plastic jar capped with a lid, and stored in a 37° C. oven for 1 week, or as otherwise indicated. Water in each jar was decanted to a separate 30 ml plastic beaker. The specimen in the jar was washed with 1 ml deionized water, and the water rinse was added to the respective beaker. The specimen was again suspended in the jar, and 10 ml of fresh deionized water was added to the jar and the jar was put back in the 37° C. oven until the next measurement. The solution was diluted with 11 ml low level TISAB* solution and fluoride was measured using an Accumet model 925 pH/mv/ISE meter available from Fischer Scientific. (The electrode used in the apparatus comprised an Orion Research electrode identified as No. 960,900.)
*TISAB=Total Ionoic Strength Adjustor Buffer available from Orion Research, Cambridge, Mass.

EXAMPLE 6—Accelerated Method

Soxhlet Method 1:

Four 1×20 mm discs of each material were made substantially as described in Example 5 and were conditioned to a constant weight. The initial average weight in grams was recorded. Two specimens were placed in each thimble of the duplicate setups. The setup consist of a 500 ml boil flask, soxhlet containing the thimble with specimens, and a Friedrichs condenser. The flask was charged with 300 ml of deionized water to be exchanged every two hours until 24 hours of test time had been accumulated. The setup was heated by an electric heating mantel to obtain a boil.

Using an ion selective electrode as described above, the fluoride concentration (PPM) was determined for each 2 hour sample., The average PPM of the duplicates were recorded.

Same as method 1 except the water was changed every 24 hours for a week.

EXAMPLE 7—EBPADMA Composite containing radiopaque fluoride leachable filler XT A composite was prepared as described in Examples 3 and 4 using the resin of Example 2, except that the silanated milled Barium glass was replaced by a radiopaque fluoride leachable filler identified as XT glass having the following approximate composition:

| | |
|---|---|
| $SiO_2$ | 47.3% |
| $Al_2O_3$ | 5.7% |
| $B_2O_3$ | 9.8% |
| BaO | 33.6% |
| F | 5.3% |
| | 101.7% |

The glass filler was shaded according to the following composition:
98.65% XT glass
0.05% iron oxide yellow
1.3% R-972 silica (Degussa)

EXAMPLE 8—EBPADMA Composite containing radiopaque fluoride leachable filler WP A composite was prepared as described in Examples 3 and 4 except that the silanated milled Barium glass was replaced by a radiopaque flouride leachable glass filler identified as WP glass having the following approximate composition:

| | |
|---|---|
| $SiO_2$ | 47.4% |
| $Al_2O_3$ | 8.0% |
| $B_2O_3$ | 8.3% |
| BaO | 29.3% |
| F | 4.6% |
| | 97.6% |

The glass filler was shaded according to the following composition:

| | |
|---|---|
| Silanated WP - ball milled 72 hours) | 98.53% |
| Red conc. (1% dispersed on WP) | 0.016% |
| Yellow conc. (10% dispersed on WP) | 0.032% |
| Black conc. (0.07% dispersed on WP) | 0.092% |
| $TiO_2$ conc. (10% dispersed on WP) | 0.028% |
| Tullanox 300 (Silica) | 1.3% |

The composite comprised 24.79% resin, as described in Example 2, and 75.21% WP glass filler.

EXAMPLE 9—EBPADMA Composite containing sodium fluoride

A composite was prepared as described in Example 4 except that 5% of the silanated milled Barium glass was replaced with sodium fluoride

EXAMPLE 10

A. Physical Testing 10 samples for testing compressive strength and diametral tensile strength[1] were prepared for each Example 4 and 7-9. Half of the specimens were stored for 1 week at 37° C., while the second half were subjected to one week extraction using the Soxhlet Method 2 described above. At the end of one week, the compressive strength and diametral strength values were calculated after breaking the specimens as per ADA specification #27 on an Instron Universal Testing Machine, Model 1123. (Instron Corp., Canton, Mass.). The results are tabulated in Table 1.

[1]Prepared as described for ADA Specification #27. Direct filling resins.

TABLE 1

| | Diametral Tensile (PSI) | | Compressive Strength (PSI) | |
|---|---|---|---|---|
| Materials | 37° $H_2O$, 1 wk | Soxhlet Extraction 1 wk | 37° $H_2O$, 1 wk | Soxhlet Extraction 1 wk |
| EXAMPLE 4 | 2773 (±150) | 3770 (±550) | 40,418 (±7281) | 46,955 (±2679) |
| EXAMPLE 7 | 5097 (±1457) | 6077 (±1498) | 59,625 (±896) | 60,649 (±3335) |
| EXAMPLE 8 | 3263 (±797) | 3454 (±821) | 50,080 (±1833) | 53,856 (±3559) |
| EXAMPLE 9 | 4272 (±537) | 2324 (±535) | 44,922 (±3331) | 48,888 (±1324) |

The above results demonstrate that under these accelerated conditions, the composite containing sodium fluoride (EXAMPLE 9) lost strength as compared to either the control (EXAMPLE 4) or those of the fluoride leachable glasses (EXAMPLE 7 and 8).

B. Fluoride Measurement

The amount of total fluoride extracted from the soxhlet procedure containing the specimens that were subsequently broken for physical testing, was analyzed as described above.

| | 1 week cumulative fluoride (PPM) |
|---|---|
| EXAMPLE 4 | 0.1999 |
| EXAMPLE 7 | 1.7002 |
| EXAMPLE 8 | 1.3810 |
| EXAMPLE 9 | 4.7768 |

The results indicated that EXAMPLE 4 contains a measurable (background) level of fluoride and that EXAMPLE 9 loses relatively speaking, much more fluoride in one week of extraction than Example 4. The composite of Example 9 also shows evidence of pitting in the surface and subsurface, which caused the sample to appear substantially opaque. This was not evident in EXAMPLES 4, 7 and 8.

EXAMPLE 11

Three materials were evaluated for fluoride release comparing the static and the accelerated method in an attempt to correlate the two procedures.

Material A

| | WT. (g) | % WT |
|---|---|---|
| DPEPAP[1] | 71.85 | 2.42 |
| UDMA[2] | 1,656.9 | 58.15 |
| BHT | 9.3 | 0.33 |
| LTS[3] | 3.0 | 0.11 |
| CQ | 6.75 | 0.24 |
| MEM[4] | 31.50 | 1.11 |
| MDEA | 11.25 | 0.39 |
| Aerosil R-972 (Degussa) | 20.0 | 0.70 |
| Cab-O-Sil TS 720 (Cabot Corp.) | 7.2 | 0.25 |
| 1% Silanated Barium Sulfate | 565.50 | 19.85 |
| Silanated Milled Barium Alumino Borosilicate Glass | 329.6 | 11.57 |
| Sodium Fluoride | 136.5 | 4.79 |
| Total | 2849.35 | 100.01 |

[1]DPEPAP — Dipentaerythritol pentaacrylate phosphate
[2]Reaction product of HPMA (hydroxypropyl methacrylate) and TMDI, made as described in U.S. Pat. No. 4,721,735.
[3]LTS — Lithium toluenesulfinate
[4]MEM — 2-N-Morpholinoethyl methacrylate Material B Fuji Glass Inonmer, G.C. Dental Corp. (Known to contain alkali metal containing glasses, polyacrylic acid, etc.

Material C

Material C comprises a self cured composite which is activated by combining a catalyst resin component with a base resin component.

|  | RVH 11-161 - | |
|---|---|---|
|  | (Catalyst) 2 | (Base) 4 |
| UDMA | 43.152 | 43.152 |
| NCO resin | 0.00 | 0.112 |
| CQ | 0.00 | 0.221 |
| DHEPT[1] | 0.00 | 0.221 |
| EDAB[2] | 0.00 | 0.353 |
| BHT | 0.066 | 0.022 |
| BPO[3] | 0.882 | 0.00 |
| Aerosil R-972 | 2.300 | 2.30 |
| Silanated XT glass | 53.600 | 53.32 |
| Iron oxide yellow (as described in Example 3) | 0.00 | 0.150 |
| Iron oxide red (as described in Example 3) | 0.00 | 0.130 |
| Flublau | 0.00 | 0.088 |
| Uvinul M-40 | 0.00 | 0.044 |
|  | 100.000 | 100.113 |

[1] Dihydroxyethyl paratoluidine
[2] Ethyl-4-dimethylaminobenzoate
[3] Benzoylperoxide
[4] 72 hour milled It was demonstrated (see Table 2) that one twenty-four hour extraction cycle with the soxhlet extractor was roughly equal to one year of static testing. Further, the release from the XT cement was very consistent from day to day, avoiding the initial burst effect of release noted in composites in which a fluoride filler was used as a source of fluoride. With the sodium fluoride containing material (material B) and glass ionomer, surface cracks and defects (pitting) were apparent. Surface cracks and defects were absent from the XT containing material.

TABLE 2

STATIC VS SOXHLET FLUORIDE RELEASE
Average Cumulative mg of Fluoride/g of Sample

|  | Material A | Material B | Material C |
|---|---|---|---|
| Static Weeks |  |  |  |
| 5 | 1189.64 | 5431.95 | 129.80 |
| 10 | 1919.39 | 7992.54 | 181.42 |
| 15 | 2445.06 | 9617.78 | 221.68 |
| 20 | 2847.36 | 10867.01 | 255.14 |
| 25 | 3159.54 | 11778.99 | * |
| 30 | 3433.03 | 12717.62 | * |
| 35 | 3673.58 | 13750.17 | * |
| 40 | 3891.52 | 14559.14 | * |
| 45 | 4086.30 | 15344.98 | * |
| 50 | 4273.33 | * | * |
| Soxhlet Hours |  |  |  |
| 2 | 1932.06 | 5282.84 | 62.08 |
| 4 | 2776.66 | 6859.18 | 103.26 |
| 6 | 3098.61 | 8159.15 | 139.18 |
| 8 | 3320.59 | 9673.25 | 172.47 |
| 10 | 3487.51 | 10338.18 | 205.40 |
| 12 | 3630.02 | 10973.92 | 235.88 |

TABLE 2-continued

STATIC VS SOXHLET FLUORIDE RELEASE
Average Cumulative mg of Fluoride/g of Sample

|  | Material A | Material B | Material C |
|---|---|---|---|
| 14 | 3849.51 | 12743.33 | 264.81 |
| 16 | 4234.68 | 13383.47 | 299.45 |
| 18 | 5012.80 | 14012.54 | 334.06 |
| 20 | 5454.95 | 14492.86 | 365.21 |
| 22 | 5824.56 | 14974.86 | 393.70 |
| 24 | 6367.75 | 15264.45 | 421.80 |

* Represents data in progress or not available.

The soxhlet method is very effective at accelerating the release of fluoride. But it is not possible to say that X number of hours will always equal Y number of weeks of static release for all materials. This is due to the fact that different materials have different rates of solubility. In favor of the soxhlet method, 24 hours continuous extraction is at least equal to or greater than one year of static release. Using the every 2 hour exchange method, a profile of the release rate can be obtained which is very similar to one year of static release of fluoride. The soxhlet method(s) has potential for predicting fluoride cumulative release from composites.

EXAMPLE 12

The tensile and compressive strength of several commercially produced restoratives were compared with comparable compositions in which at least a portion of the filler was replaced with NaF, XT glass and $SrF_2$. The materials were evaluated for mechanical properties and fluoride release after being subjected to extraction for 7 days in the soxhlet extraction apparatus. Material 1, which served as a control, was PRISMA-Fil (shade light, batch number 0920881) a product of the L. D. Caulk, Company, Milford, DE. Material 2 was Fluorever (batch number 020798) a product of Essential Dental Systems, Long Island, N.Y. Material 3 was a modification of Ful-Fil ®, a product of the L. D. Caulk Company, in which part of the filler was replaced by NaF and which was prepared as described in U.S. Pat. No. 4,514,174. Material 3 was prepared by substitution of 5% by weight of the silanated milled Barium Boron Aluminum Silicate glass filler (Corning Glass 7724) with sodium fluoride. The net filler loading of Material 3 remained the same as described in U.S. Pat. No. 4,514,174. Material 4 represented a composition identical to PRISMA-Fil except all of the filler was replaced with silanated Milled XT glass. Material 5 was a modification of PRISMA-Fil where 5% of the silanated filler was replaced with an equivalent amount of strontium fluoride. The results of the comparison are illustrated in Table 3.

The results seen in Table 3 are illustrated graphically in Graph 1. The graph illustrates that the restorative employing XT glass does not show as large an initial release burst of F as do the restorations containing fluoride salts, and maintains a higher level of fluoride release over an extended period of time. While showing a higher sustained fluoride release, as can be seen in Table 3, the restorative containing the XT glass also shows much higher tensile and compressive strengths than do the restoratives containing the fluoride salts.

TABLE 3

7-Day Soxhlet Extraction of PRISMA Fil Composites
Daily Water change for Cumulative F - RVH 11-192

7 Days @ 37° C.    7 Days Soxhlet    7 Days @ 37° C.    7 Days Soxhlet

TABLE 3-continued

| | | Tensile | Tensile | Compression | Compression |
|---|---|---|---|---|---|
| 1. PRISMA-fil (L) #0920881 Control (PSI) | x | 6161.4 | 3955.2 | 50,305.4 | 50,055.6 |
| | s | 1541.0 | 515.5 | 847.7 | 4,773.1 |
| | n | 5 | 5 | 5 | 5 |
| 2. FluorEver #020798 | x | 2643.3 | 2471.3 | 29,356.6 | 23,772.7 |
| | s | 477.2 | 262.6 | 922.6 | 1,582.8 |
| | n | 5 | 5 | 5 | 5 |
| 3. FUL-Fil with 5% NaF | x | 2165.3 | 1200.2 | 39,319.7 | 30,418.9 |
| | s | 844.4 | 282.6 | 6,345.4 | 1,090,3 |
| | n | 5 | 6 | 5 | 5 |
| 4. PRISMA-fil with XT | x | 4305.8 | 5050.7 | 44,996.7 | 45,561.4 |
| | s | 1197.3 | 2309.8 | 1,167.0 | 4,380.0 |
| | n | 5 | 5 | 5 | 5 |
| 5. PRISMA-fil with 5% SrF$_2$ | x | 4079.3 | 3893.3 | 43,881.1 | 39,117.4 |
| | s | 537.6 | 635.0 | 1,564.5 | 5,877.8 |
| | n | 5 | 5 | 5 | 5 | x = mean value
s = standard deviation
n = number of specimens tested

| | Fluoride Release Data: | | | | |
|---|---|---|---|---|---|
| | 1 | 2 | 3 | 4 | 5 |
| Initial Specimens Wt. g | 4.6708 | 3.9994 | 4.5643 | 3.0535 | 4.3545 |
| Days of Sox Extraction | PPM (ugF/g) | PPM (ugF/g) | PPM (ugF/g) | PPM (ugF/g) | PPM (ugF/g) |
| Day 1 | .07054/4.5 | 17.388/1341.2 | 9.4988/624.3 | 1.8791/184.6 | .5504/37.9 |
| Day 2 | .06158/4.0 | 7.9736/615.0 | 8.8527/581.9 | .5718/56.2 | .3975/27.4 |
| Day 3 | .056/3.6 | 7.8170/602.9 | 9.9606/659.7 | .5689/55.9 | .4169/28.7 |
| Day 4 | .06285/4.0 | 5.9121/456.0 | 6.2679/412 | .5257/51.6 | .4134/28.5 |
| Day 5 | .06502/4.2 | 5.8407/450.5 | 7.6324/501.7 | .6652/65.4 | .5343/36.8 |
| Day 6 | .06172/4.0 | 4.500/347.1 | 5.5920/367.5 | .4650/45.7 | .4428/30.5 |
| Day 7 | .06022/3.9 | 3.3920/261.6 | 4.3008/282.7 | .4630/45.5 | .3179/21.9 |
| Cumulative F-ion release | .04379/28.2 | 42.8234/4074.3 | 52.1052/3424.8 | 5.1387/504.9 | 3.0732/211.7 |

Figure 2:
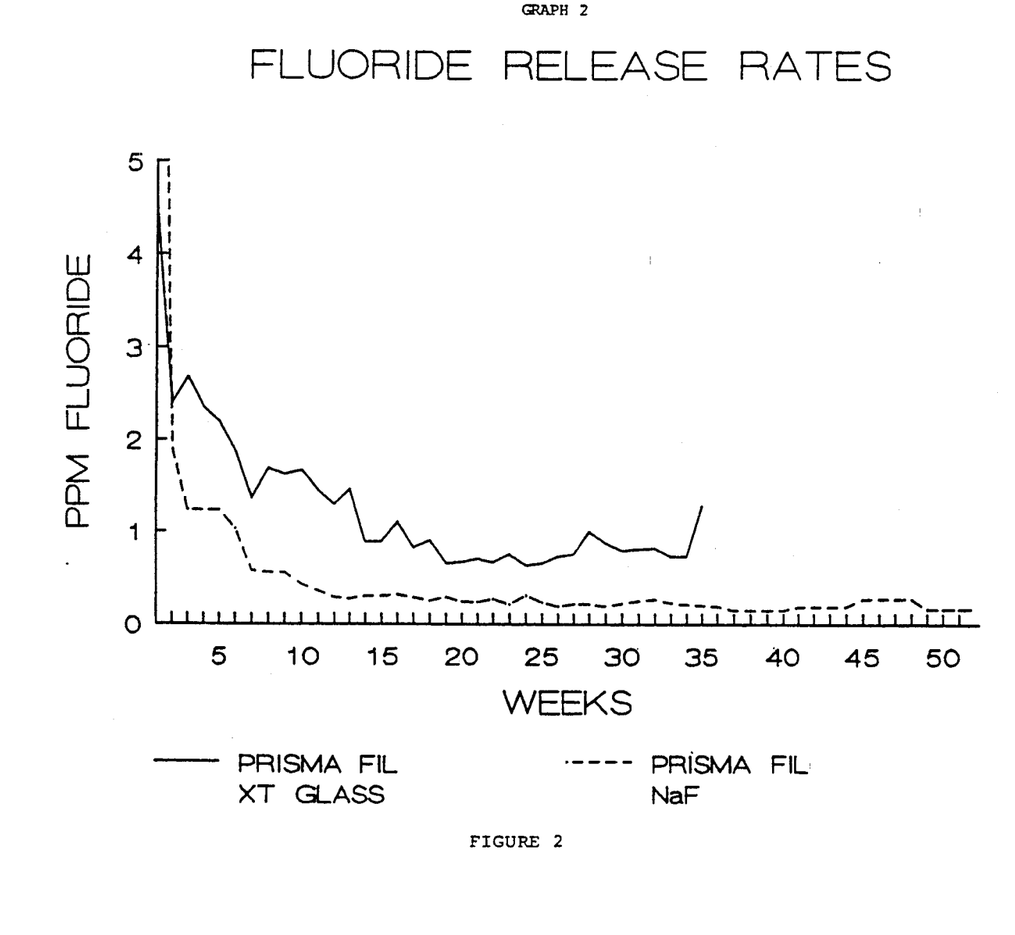
FIG. 2 (Graph 2) is a schematic representation of fluoride release rates in accordance with the invention.

A more direct comparison of the fluoride release is shown in Graph 2, where the fluoride release properties of PRISMA-FIL containing NaF in the filler is compared with the fluoride release properties of PRISMA-FIL in which the usual filler is replaced by XT glass.

Other modifications and ramifications of the present invention will become apparent to those skilled in the art upon a reading of this disclosure. It is to be understood that such modifications and ramifications are intended to be included within the scope of this invention.

What is claimed is:

1. A dental composite composition comprising; photoactivated resin suitable for a dental restorative and translucent, phase separated, fluoride-containing glass wherein the phase separated droplets do not exceed about 1400 angstrom in size and wherein upon exposure to an aqueous environment, fluoride ions will be released therefrom at a controlled, relatively constant rate over a substantial period of time, but with essentially no development of porosity or other physical breakdown effect, and which can be melted and formed with relatively low volatilization of fluorine, said glass being essentially free of alkali metal oxides and heavy toxic metals and consisting essentially, expressed in terms of weight percent of: SiO$_2$: 40-56; BaO: 15-35; Al$_2$O$_3$: 4-12; B$_2$O$_3$: 5-12: F: 2-20; ZrO: 0-7; SrO: 0-18.

2. A method of making a dental composite restorative composition, comprising:
providing a resin suitable for use in a dental restorative and an inorganic filler comprising nonalkali, radiopaque glass containing extractable fluoride, said glass being translucent, phase separated, fluoride-containing glass wherein the phase separated droplets do not exceed about 1400 angstrom in size and wherein upon exposure to an aqueous environment, fluoride ions will be released therefrom at a controlled, relatively constant rate over a substantial period of time, but with essentially no development of porosity or other physical breakdown effect, and which can be melted and formed with relatively low volatilization of fluorine, said glass being essentially free of alkali metal oxides and heavy toxic metals and consisting essentially, expressed in terms of weight percent of: SiO$_2$: 41.4-55.9; BaO: 24.7-33.6; Al$_2$O$_3$: 5.6-11; B$_2$O$_3$: 6.5-10.3; F: 3-6 and
forming said composition into a dental composite restorative adapted to provide at least 0.5 ppm of fluoride through leaching into a static aqueous medium at about 37° C. replaced weekly over a 30 week period.

3. A method of extracting fluoride form a dental composite restorative composition, comprising:
providing a blend of at least 10% by weight of polymerizable resin suitable for use in a dental restorative and from 20 and 90% by weight of an inorganic filer comprising nonalkali, silantable, radiopaque glass containing BaO and fluoride, said glass being translucent, phase separated, fluoride-containing glass wherein the phase separated droplets do not exceed about 1400 angstrom in size and wherein upon exposure to an aqueous environment, fluoride ions will be released therefrom at a controlled, relatively constant rate over a substantial period of time, but with essentially no development of porosity or other physical breakdown effect, and which can be melted and formed with relatively low volatilization of fluorine, said glass being essentially free of alkali metal oxides and heavy toxic metals and consisting essentially, expressed in terms of weight percent of: SiO$_2$: 41.4-55.9; BaO: 24.7-33.6; Al$_2$O$_3$: 5.6-11; B$_2$O$_3$: 6.5-10.3; F: 3-6 and
forming said composition into a dental composite restorative adapted to provide at least 0.5 ppm of fluoride through leaching into a static aqueous medium at about 37° C. at a rate sufficient to maintain from about 0.5 to about 2.0 ppm fluoride in said medium over a 20 week period during which said medium is replaced weekly.

4. The composition of claim 1 wherein said resin and glass comprises a matrix wherein said resin is chemically bonded to said inorganic filler, and wherein said matrix is adapted to slowly release fluoride ion when said matrix is in the oral cavity without significantly reducing the strength and physical integrity of said matrix.

5. The composition of claim 1 wherein said inorganic filler is essentially free of alkali metal oxides and heavy toxic metals and consists essentially of by weight 41.4–55.9% $SiO_2$, 24.7–33.6% BaO, 5.6–11% $Al_2O_3$, 6.5–10.3% $B_2O_3$, and 3–6% F.

6. The composition of claim 1 wherein said glass comprises 4–8% $Al_2O_3$.

7. The composition of claim 1 wherein said fluoride is provided in said glass by the presence of $SrF_2$, $AlF_3$, or $BaF_2$, or a mixture thereof in the materials used in the preparation of said glass.

8. The composition of claim 1 wherein said resin is hardenable by free radical polymerization and comprises:
   (a) binder resin comprising the reaction product of at least one vinyl ester of a polyglycidyl ether having secondary hydroxyl groups and at least one isocyanate reactant, said isocyanate reactant and said vinyl ester reacting through said secondary hydroxyl groups;
   (b) a polymerizable acrylic diluent monomer; and
   (c) a free radical polymerization catalyst, said diluent being present in an amount such that said composition has a viscosity suitable for use in dental applications.

9. The composition of claim 1 wherein said resin comprises isocyanate having ethylenic unsaturation.

10. The composition of claim 1 wherein said resin comprises a photosensitive catalyst system.

11. The composition of claim 1 which comprises from about 20% to about 90% by weight of said glass.

12. The composition of claim 1 wherein said resin comprises Bis-GMA.

13. The composition of claim 1 wherein said resin comprises isocyanatoethyl methacrylate.

14. The composition of claim 1 wherein said resin comprises triethyleneglycol diemthacrylate, 1,6-Hexanediol dimethacrylate, or ethoxylated bisphenol-A-dimethacrylate.

15. The composition of claim 1 wherein said resin component comprises the reaction product of a vinyl ester of a polyglycidyl ether having secondary hydroxyl groups, a first isocyanate reactant containing ethylenic unsaturation and a second isocyanate reactant which is diisocyanate, said vinyl ester and said first and second isocyanate reactants being reacted through said secondary hydroxyl groups.

16. The composition of claim 1 wherein said resin comprises Bis-GMA, isocyanathoetyhl methacrylate or trimethylhexamethylene diisocyanate.

17. The composition of claim 1 wherein said resin comprises the reaction product of a second vinyl ester of a polyglycidyl ether having secondary hydroxyl groups and a diisocyanate reacted through said secondary hydroxyl groups.

18. The composition of claim 1 wherein said resin comprises Bis-GMA and a diisocyanate selected from the group consisting of trimethylhexamethylene diisocyanate, hexamethylene diisocyanate, and phenylene diisocyanate.

19. The composition of claim 1 wherein said resin comprises a diisocyanate.

20. The composition of claim 1 wherein said resin comprises trimethylhexamethylene diisocyanate, hexamethylene diisocyanate, and phenylene diisocyanate.

21. The composition of claim 1 wherein said inorganic filler comprises, by weight, from about 35 to about 64% of silanated barium glass having a mean particle size of from about 5 to about 9 microns, from about 20 to about 50% of a silanated barium glass having a mean particle size of from about 2 to about 5 microns, and from about 5 to about 15% of a silanated submicron silica.

22. The composition of claim 1 wherein said glass is present in said composition in an amount of from about 50% to about 80% by weight.

23. The composition according to claim 1 wherein up to one-half on a molar basis of BaO is replaced with SrO.

24. The composition according to claim 1 wherein up to one-third on a molar basis of BaO is replaced with ZnO.

25. The composition according to claim 1 wherein said heavy toxic metals are selected from the group consisting of arsenic, cadmium, lead and mercury.

26. The composition according to claim 1 wherein said fluoride is included in the composition through the use of a batch material selected from the group of $AlF_3$ and $BaF_2$.

27. A dental composite restorative composition comprising
   (a) a resin suitable for use in a dental restorative, and
   (b) an inorganic filler particle having a mean particle size less than 9 microns comprising a non alkali, silantable, radiopaque glass containing extractable fluoride, said fluoride comprising from about 1 to about 20 percent by weight of said composition said glass being translucent, phase separated, fluoride-containing glass wherein the phase separated droplets do not exceed about 1400 angstrom in size and wherein upon exposure to an aqueous environment, fluoride ions will be released therefrom at a controlled, relatively constant rate over a substantial period of time, but with essentially no development of porosity or other physical breakdown effect, and which can be melted and formed with relatively low volatilization of fluorine, said glass being essentially free of alkali metal oxides and heavy toxic metals and consisting essentially, expressed in terms of weight percent of: $SiO_2$: 41.4–55.9; BaO: 24.7–33.6; $Al_2O_3$: 5.6–11; $B_2O_3$: 6.5–10.3; F: 3–6;

28. The composition of claim 27 wherein said fluoride comprises from about 2 to about 15 percent by weight of said composition.

29. The composition of claim 27 wherein said fluoride comprises from about 2 to about 7 percent by weight of said composition.

* * * * *